United States Patent
Macy, Jr.

(10) Patent No.: US 9,060,752 B2
(45) Date of Patent: Jun. 23, 2015

(54) METHODS AND DEVICES FOR ASEPTIC IRRIGATION, URINE SAMPLING, AND FLOW CONTROL OF URINE FROM A CATHETERIZED BLADDER

(75) Inventor: Bradford Macy, Jr., Concord, CA (US)

(73) Assignee: Hospi Corporation, Newark, CA (US)

( * ) Notice: Subject to any disclaimer, the term of this patent is extended or adjusted under 35 U.S.C. 154(b) by 240 days.

(21) Appl. No.: 13/414,205

(22) Filed: Mar. 7, 2012

(65) Prior Publication Data

US 2012/0232503 A1 Sep. 13, 2012

Related U.S. Application Data (60) Provisional application No. 61/464,705, filed on Mar. 8, 2011.

(51) Int. Cl.
*A61M 27/00* (2006.01)
*A61B 10/00* (2006.01)

(52) U.S. Cl.
CPC .................... *A61B 10/007* (2013.01)

(58) Field of Classification Search
CPC ............. A61B 10/007; A61M 39/26; A61M 2039/261; A61M 2039/262; A61M 2039/263; A61M 39/045
USPC ................. 604/540, 544, 533–537, 539, 284; 137/875, 885
See application file for complete search history.

(56) References Cited

U.S. PATENT DOCUMENTS

| | | | |
|---|---|---|---|
| 1,234,582 A | 7/1917 | Trueblood | |
| 3,513,849 A * | 5/1970 | Vaillancourt et al. | 604/256 |
| 3,699,964 A * | 10/1972 | Ericson | 604/33 |
| 3,707,972 A * | 1/1973 | Villari et al. | 604/249 |
| 3,835,835 A | 9/1974 | Thompson et al. | |
| 3,965,910 A * | 6/1976 | Fischer | 604/249 |
| 4,476,866 A | 10/1984 | Chin | |
| 4,685,910 A | 8/1987 | Schweizer | |
| 4,723,943 A | 2/1988 | Spencer | |
| 5,522,806 A | 6/1996 | Schonbachler et al. | |
| 6,165,168 A | 12/2000 | Russo | |
| 6,183,413 B1 | 2/2001 | Migachyov | |
| 6,245,048 B1 * | 6/2001 | Fangrow et al. | 604/249 |
| 6,663,590 B2 * | 12/2003 | Blatter | 604/103.01 |

(Continued)

FOREIGN PATENT DOCUMENTS

| | | |
|---|---|---|
| EP | 2140903 A1 | 1/2010 |
| LU | 58599 A1 | 8/1969 |

(Continued)

*Primary Examiner* — Jackie T Ho
*Assistant Examiner* — Mark K Han
(74) *Attorney, Agent, or Firm* — Shay Glenn LLP (57) ABSTRACT

A urinary catheter connector system having a housing; a catheter connector port supported by the housing and configured to attach to a urinary catheter; a urine exit port supported by the housing and configured to connect to a urine collection device; an irrigation port supported by the housing and configured to receive an irrigation syringe; a channel in the housing fluidly connecting the catheter connector port, the urine exit port and the irrigation port; and a valve supported by the housing and adapted to cooperate with the irrigation syringe to shut off flow of fluid and air to the urine exit port when the irrigation syringe is inserted and allow for flow of fluid and air to the urine exit port when the irrigation syringe is removed. The invention also includes methods of using the system.

12 Claims, 7 Drawing Sheets

(56) References Cited

U.S. PATENT DOCUMENTS

| | | |
|---|---|---|
| 6,913,244 B1 | 7/2005 | Atkinson et al. |
| 7,056,301 B2 | 6/2006 | Liu |
| 7,056,308 B2 * | 6/2006 | Utterberg ............ 604/256 |
| 7,150,740 B2 | 12/2006 | Bennett et al. |
| 7,850,677 B2 | 12/2010 | Blake et al. |
| 8,075,533 B2 | 12/2011 | Lee |
| 8,353,895 B2 * | 1/2013 | Russo ............ 604/533 |
| 2003/0195478 A1 | 10/2003 | Russo |
| 2006/0064065 A1 | 3/2006 | Russo |
| 2010/0292672 A1 | 11/2010 | Lee |
| 2012/0277664 A1 | 11/2012 | Macy, Jr. |

FOREIGN PATENT DOCUMENTS

| | | |
|---|---|---|
| RU | 1806770 A1 | 4/1993 |
| RU | 2116802 C1 | 8/1998 |
| WO | WO 96/40359 A1 | 12/1996 |

* cited by examiner

METHODS AND DEVICES FOR ASEPTIC IRRIGATION, URINE SAMPLING, AND FLOW CONTROL OF URINE FROM A CATHETERIZED BLADDER

CROSS REFERENCE TO RELATED APPLICATIONS

This application claims the benefit under 35 U.S.C. §119 of U.S. Provisional Patent Appl. No. 61/464,705 filed Mar. 3, 2011, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This invention relates to methods, systems, and apparatuses to assist with the irrigation, urine sampling, and drainage of the catheterized bladder, and more particularly, but not limited to, aseptic methods, systems, and apparatuses to assist with improved irrigation, urine sampling, and drainage of the catheterized bladder.

BACKGROUND

Existing catheter technology results in numerous health and safety issues for patients, medical personnel, and the community at large. The technology of indwelling urinary catheters has barely changed over the last 50 years. Improvements in existing urinary catheter systems are highly desirable. A urinary catheter drainage system is made up of the catheter itself which is inserted into the bladder, and the urine collection device which attaches to the catheter with a tubing and collects the urine into some type of receptacle depending on its purpose. One example of a urine collection device is a bedside drainage bag, which is usually a tube connected to the catheter leading to a large bag that hangs on the bedside to collect the urine. Another example is a leg bag which is worn when a patient is up and around and is a shorter tube attached to a smaller bag which is attached to the leg and collects urine.

The complications associated with catheterization include, catheter associated urinary tract infections (CAUTI's), blockage, (due to struvite or biofilm formation), bladder atony, (causing a short term or permanent inability to void), bladder spasms, and thickening of the bladder wall from long term use.

In addition to direct patient complications, there are numerous safety issues related to current catheter systems both in the inpatient setting, and the home health setting. Present systems put clinicians at risk of occupational injury related to bio-hazardous waste exposure. Clinicians are frequently sprayed with urine when attempting to irrigate clogged catheters when pressure from the irrigation syringe causes swelling of the catheter and spray back to occur. Because the current available catheter technology demands that the catheter be disconnected from the urine collection device in order to irrigate the system, leaking or spilling of urine occurs during these procedures. When these spills and splashes occur, clinicians, other patients, and the community at large are put at risk for cross contamination and the spread of infection, including antibiotic resistant pathogens.

In summary, most of the problems listed above arise, at least in part, from two primary problems with existing catheter systems: (1) Current catheter systems do not allow for the maintenance of a closed, aseptic system; and (2) Current catheter systems do not allow the bladder to fill and empty in a normal fashion.

About 30% of CAUTI's are shown to be caused by intraluminal bacterial biofilm formation. The primary way bacteria enter the inner lumen to cause infection is by entering the drainage end of the catheter and ascending the inner lumen to the bladder. The 2009 CDC Healthcare Infection Control Practices Advisory Committee (HICPAH) recommended a closed urinary drainage system with all catheters as a high priority recommendation, essential for all healthcare organizations caring for patients with catheters. They found both older and more recent data indicating that disconnection of the urine collection device from the catheter is a risk factor for bacteriuria.

In order to maintain a closed urinary drainage system, the catheter must not be disconnected from the urine collection device. The most common reason for disconnecting the catheter from the urine collection device is when the catheter needs to be irrigated. Many catheters need to be irrigated several times a day exposing the patient to infection and the clinician to bio-hazardous waste up to several times a day.

In order to address the specific problem associated with closed irrigation of a catheter, Russo U.S. Patent Application Pub. No. US 2006/0064065 discloses a closed system irrigation connector for urinary catheters which allows for a closed irrigation of the catheter wherein a silicone diaphragm opens when an irrigation device is attached, and closes when it is removed. But the device of Russo does not provide for an aseptic irrigation procedure. In order to maintain an aseptic closed system, anything entering said system must be free of bacteria. This means that the system must have entrance portals that are closed while not being accessed and that are fully sanitizable prior to access.

In order to effectively sanitize a surface, the surface must be easily and fully accessible to apply the needed friction and anti-infective agent. The surface must not have crevices or difficult to reach places where bacteria can the friction and antimicrobial agent. The plastic entrance port disclosed by Russo does not have a flat, easily sanitizable surface, but has a crevice that cannot be effectively sanitized. Bacteria hiding on this un-sanitizable surface can enter the system during irrigation and infect the patient.

The second major problem with current catheter systems is that they drain the bladder constantly, not allowing it to fill and empty in a normal manner. This leaves a pool of concentrated, stagnant urine in the neck of the bladder below the drainage holes on the catheter. This stagnant urine serves to create a perfect breeding ground for bacteria.

Catheter blockage is another problem with "constant drain" catheter systems caused by the buildup of biofilm and salt crystals at the opening of the catheter. Much like a stalactite, the high pH, high mineral fluid in the neck of the bladder provides the perfect environment for this to occur.

Bladder spasms can be caused by several factors. The most frequent cause is CAUTI as already discussed above. The bladder wall becomes irritated and even swells and spasm occurs. The loss of normal stretching and contracting of the detrusor can also cause spasm. Irritation from highly concentrated, and high pH urine could also be factor. Bladder wall thickening has also been observed in long-term catheterizations and may be a result of the increasing. Catheter related bladder atony is another complication associated with not allowing the bladder to fill and empty. When the bladder no longer fills and empties in a normal fashion, the detrusor muscle can atrophy causing a temporary or even permanent inability to void after catheterization. These problems could be solved, at least in part by allowing the bladder to fill and drain in a more normal fashion.

Many types of valved catheters and universal connections exist which allow for intermittent draining and retention of the bladder. None of the prior art in this area discloses sanitizable surfaces on entry ports leading from the outside to the inside of the closed urinary drainage system. These systems complicate the problem by introducing bacteria into what should be a closed system. A system, method, and apparatus is needed that allows for aseptic irrigation and urine sampling while maintaining a closed system, and allows for control of urine flow, allowing the bladder to fill and empty as needed or prescribed.

SUMMARY OF THE DISCLOSURE

A system, method, and apparatuses for improved aseptic irrigation, urine sampling, and flow control of urine from the catheterized bladder are disclosed. The disclosed invention, also referred to for the purposes of easy reference only, as a Port and Valve Assembly, allows for aseptic irrigation and urine sampling of the catheterized bladder without disconnecting the catheter from the drainage bag by providing a sanitizable self closing port and allowing for bypassing of the drainage bag during irrigation. An irrigation syringe, irrigating device or urine sampling device can be inserted into a self closing port on the apparatus to irrigate or urine sample the bladder without disconnection of the catheter from the urine collection device, and the bladder can be irrigated or urine sampled while maintaining a closed, aseptic system. When the syringe is removed the port closes. The flat closed surface of the port is easily sanitizable with standard medical sanitizer such as 70% alcohol so bacteria cannot enter the system when a device is attached. This allows for aseptic access to the interior of the urinary catheter system so that irrigation can be performed without contamination of the urinary drainage system by bacteria, or exposure to body fluids and infectious waste.

Another aspect of the invention employs an inner mechanism which shuts the flow of fluid to the urine collection device while an irrigation syringe, irrigation device, or collection device is inserted in the port. This mechanism allows for effective irrigation and urine sampling of the catheter and bladder without fluid or air being shunted into or pulled from the drainage collection device. Shutting flow off from the urine collection device is essential for irrigating a catheter while attached to the urine collection device, otherwise fluid would flow into the collection device and not the catheter being irrigated. The enhanced system disclosed also makes the collection of urine samples easy by sealing the urine collection device end, and allowing for suction of urine from the bladder.

In yet another aspect, within some embodiments of the present invention, the system and apparatus has an externally controlled mechanism to shut off the flow of urine from the bladder to the urine collection device for a prescribed adjustable period of time, enabling the bladder to fill and empty in a more normal fashion. This feature is important because it allows clinicians to set the amount of time for bladder filling, without worrying about releasing the urine at a particular time, as it is done automatically, an important safety and convenience feature. This feature also allows for bladder training of patients, allowing for increased increments of time in which the bladder can fill with urine, thus slowly training the bladder to hold more urine before needing to empty.

The improved utilities of the present invention could decrease the chance of urinary tract infection, bladder atony, decrease the risk of blood and body fluid exposure, and greatly simplify the procedure of bladder irrigation of the catheterized patient.

One aspect of the invention provides a urinary catheter connector system having a housing; a catheter connector port supported by the housing and configured to attach to a urinary catheter; a urine exit port supported by the housing and configured to connect to a urine collection device; an irrigation port supported by the housing and configured to receive an irrigation syringe; a channel in the housing fluidly connecting the catheter connector port, the urine exit port and the irrigation port; and a valve supported by the housing and adapted to cooperate with the irrigation syringe to shut off flow of fluid and air to the urine exit port when the irrigation syringe is inserted and allow for flow of fluid and air to the urine exit port when the irrigation syringe is removed. In some embodiments, the valve has a first position in which the urine collection device is in fluid communication with the catheter connector port and a second position in which the urine collection device is not in fluid communication with the catheter connector port. The valve may be biased to the first position by, e.g., a spring. The valve may also be adapted to be moved from the first position to the second position by a syringe tip inserted into the irrigation port.

In some embodiments, the valve includes a thickening in the wall of the housing, wherein the thickening decreases the diameter of the channel and is configured to approximate the size of the tip of an irrigation syringe and to mate snugly with the irrigation syringe, wherein when the irrigation syringe is inserted into the valve, the urine collection device is not in fluid communication with the catheter connector port, and when the syringe is not inserted in the valve opening the urine collection device is in fluid communication with the catheter connection port. In some embodiments the valve has a valve seat adapt to mate with an exterior surface of the irrigation syringe to shut off the flow of fluid and air to the urine exit port when the irrigation syringe is inserted and allow for the flow of fluid and air to the urine exit port when the irrigation syringe is removed.

Some embodiments of the invention also include a valve control mechanism adapted to move the valve from the first position to the second position without inserting a device into the irrigation port. The valve control mechanism may be adapted to automatically permit the valve to move from the second position to the first position after a time period without operator intervention. In some embodiments, the valve control mechanism includes a compliant balloon.

Some embodiments of the invention have a valve control mechanism with a compliant balloon adapted to be inflated to close the valve. Some such embodiments also include a compressible fluid-filled actuation chamber, first and second passages connecting the actuation chamber with the interior of the balloon and a one-way valve disposed in the first passage to permit fluid flow from the actuation chamber into the balloon and block fluid flow from the balloon into the actuation chamber. The valve control mechanism may also have a syringe port adapted to permit inflation of the balloon by a syringe.

Some embodiments of the invention also have a pliable membrane extending over the irrigation port, the membrane having a self-sealing opening adapted to permit insertion of a syringe tip. In some embodiments, the irrigation port has an exterior surface that is flat and completely exposable to friction applied with a medical sanitizing agent so that the irrigation port is fully sanitizable. The irrigation port may connect to the channel between the catheter connection port and the urine exit port.

Another aspect of the invention provides a method of irrigating a urinary catheter including the steps of: draining urine from an indwelling urinary catheter through a catheter connector port, a channel and out through a urine exit port; simultaneously opening an irrigation port and closing off flow to the urine exit port; and injecting irrigation fluid through the irrigation port, the channel, the catheter connector port and into the catheter. In some embodiments, the irrigation port surface is sanitized prior to insertion of the irrigation syringe. In some embodiments, the method also includes the step of simultaneously closing the irrigation port and opening the urine exit port, thereby allowing urine to drain from the indwelling urinary catheter through the channel and out the urine exit port.

In some embodiments, the step of simultaneously opening the irrigation port and closing the urine exit port includes the step of moving a valve from a first position in which the urine exit port is in fluid communication with the catheter connector port to a second position in which the urine exit port is not in fluid communication with the catheter connector port. The moving step may include the step of moving the valve with a distal tip of a syringe. The method may also include the step of inserting the syringe through a self-sealing opening in the irrigation port.

In some embodiments, the step of simultaneously opening the irrigation port and closing the urine exit port includes the step of inserting a syringe through the irrigation port and into a valve. In some such embodiments, the step of simultaneously opening the irrigation port and closing the urine exit port further includes the step of seating an outside surface of the syringe in a valve seat of the valve.

Yet another aspect of the invention provides a method of operating a urinary catheter system including the following steps: establishing flow of urine from an indwelling urinary catheter through a connector and into a drainage bag; actuating a valve to stop the urine flow; and permitting the valve to automatically open after a time period without operator intervention.

In some embodiments, the actuating step includes the step of expanding a balloon to block flow through the connector. In some embodiments, the permitting step includes the step of permitting the balloon to deflate. In some embodiments, the expanding step includes the step of compressing a valve actuation chamber. In some embodiments, the expanding step includes the step of injecting fluid into the balloon with a syringe.

Still another aspect of the invention provides a method of operating a urinary catheter system including the following steps: establishing flow of urine from an indwelling urinary catheter through a connector and valve opening and into a urine drainage connector; inflating a balloon manually to stop the urine flow through the valve opening and drainage connector; and deflating the balloon manually to allow urine to flow through the valve opening and drainage connector.

Yet another aspect of the invention provides a urinary catheter system including a urinary catheter port; a urine exit port; an irrigation port configured to receive an irrigation syringe; a channel connecting the urinary catheter port, urine exit port and irrigation port; and a valve adapted to cooperate with the irrigation syringe to shut off flow of fluid and air to the urine exit port when the irrigation syringe is inserted and allow for flow of fluid and air to the urine exit port when the irrigation syringe is removed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The following description and drawings are illustrative and are not to be construed as limiting. Numerous specific details are described to provide a thorough understanding. However, in certain instances, well known or conventional details may not be described in order to avoid obscuring the description. In accordance with the present invention, a novel and improved system for aseptic irrigation and urine specimen collection from the catheterized bladder is provided.

Figure 1:
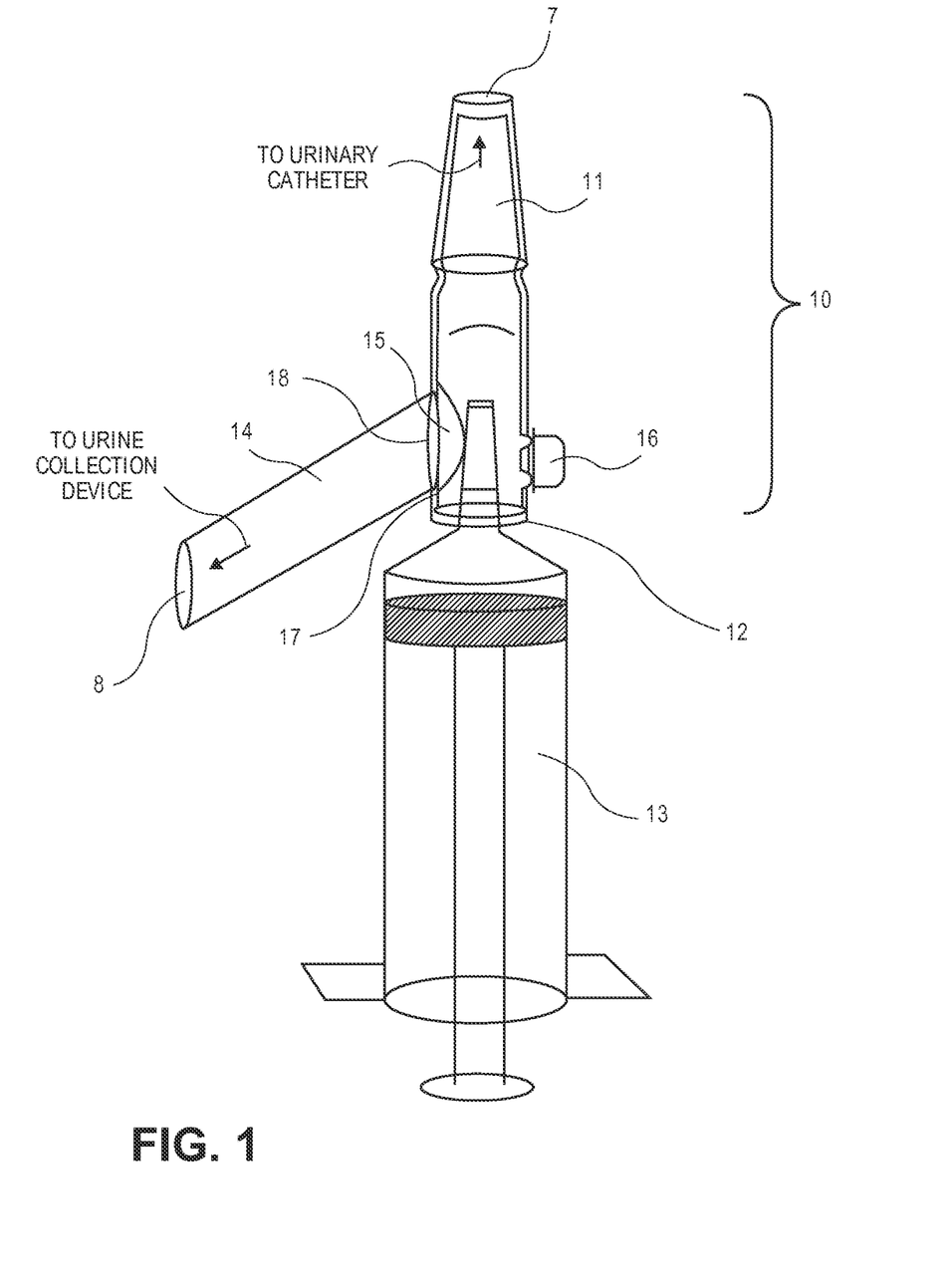
FIG. 1 is an illustration of a self closing port and valve assembly according to one embodiment of the invention showing an irrigating syringe inserted into a self closing port and bypassing the urine collection device through means of a valve, which closes flow when to urine collection device when irrigation device is attached.
Figure 2:
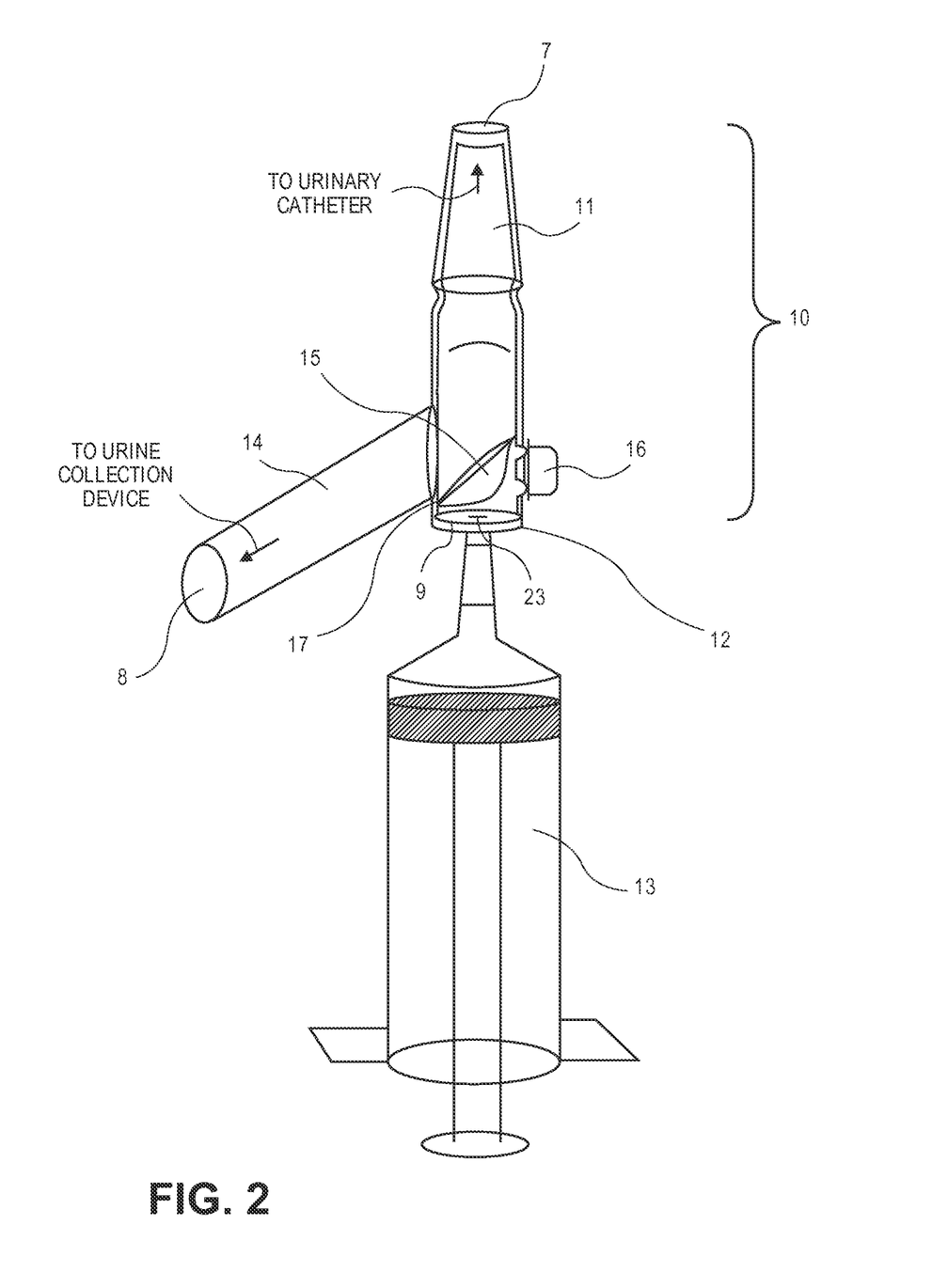
FIG. 2 is an illustration of a self closing port and valve assembly showing the device of FIG. 1 without an irrigating syringe inserted into the self closing port in which valve is open and urine can flow into urine collection device.

FIGS. 1 and 2 are illustrations of a self closing port and valve assembly 10 according to one embodiment of the present invention. Within this embodiment the device has a fully sanitizable self closing irrigation port 12 that allows a urinary catheter to remain attached to a urine collection device while being irrigated without disconnecting the urine collection device drainage tubing 14 from the urinary catheter (not shown). This allows for an aseptic, closed system, which keeps bacteria from entering the catheter and also prevents exposure to body fluids during the irrigation or sampling process.

The self closing port and valve assembly 10 could be located in numerous places on a urinary catheter drainage system. For instance, it could be a part of a urinary catheter itself. It could be a separate device that connects between the catheter and the drainage bag, or it could be a part of the urine collection device. In the embodiment of FIGS. 1 and 2, it is a part of the urine collection device, and is located at the junction between the catheter connector port 7 in the catheter connector 11 and the urine exit port 8 in the drainage tube 14 which drains urine from the catheter into the urine collection device.

In the embodiment of FIGS. 1 and 2, an internal valve 15 has a tension spring 17. The spring tension keeps the internal valve biased in a first position in which a urine exit port 18 is open to the urine drainage tube 14. Spring 17 can be, for example, a torsion spring, leaf spring or any other spring or spring-like element. Insertion of a catheter tip irrigation syringe or other similar device 13 into the self closing irrigation port 12 pushes the internal valve 15 to a second position against the urine exit port to the urine collection device drainage tube 14, closing it off and bypassing any flow to the drainage tube while keeping the irrigation port open.

In the present embodiment, the valve 15 is fashioned so that a portion of it protrudes into the path of a device 13 inserted into the self closing irrigation port 12. The device inserted into the port pushes the protruding portion of the valve in the direction of the urine exit port, closing the valve when the device is inserted into the irrigation port. This automatically shuts off the flow of fluid and air to the drainage bag allowing for irrigation of the catheter and bladder without the irrigation fluid entering the drainage tube. When the irrigation procedure is complete and the syringe 13 is removed, the spring 17 moves the valve back to the open position to allow urine to flow from the catheter, into the urine collection device and to the drainage collection receptacle.

In the embodiment of the device in FIGS. 1 and 2, a port and valve assembly 10 also has a valve control mechanism 16 to externally shut the valve 15 without the insertion of a syringe or other object into the port 12. This would allow the valve 15 to be closed even when not irrigating or collecting samples from the catheter. Keeping the valve closed would stop the flow of urine from the bladder to the urine collection device drainage tube 14, and allow the bladder to fill with urine, an important physiological function that is normally inhibited in state of the art urinary catheter systems. In some embodiments, the valve control mechanism 16 may be designed in such a way as to allow for the valve to stay closed for a specific prescribed and adjustable amount of time, allowing for the bladder to fill for a prescribed amount of time and then empty when that time period ends. Examples of the valve control mechanism are described below.

Figure 3:
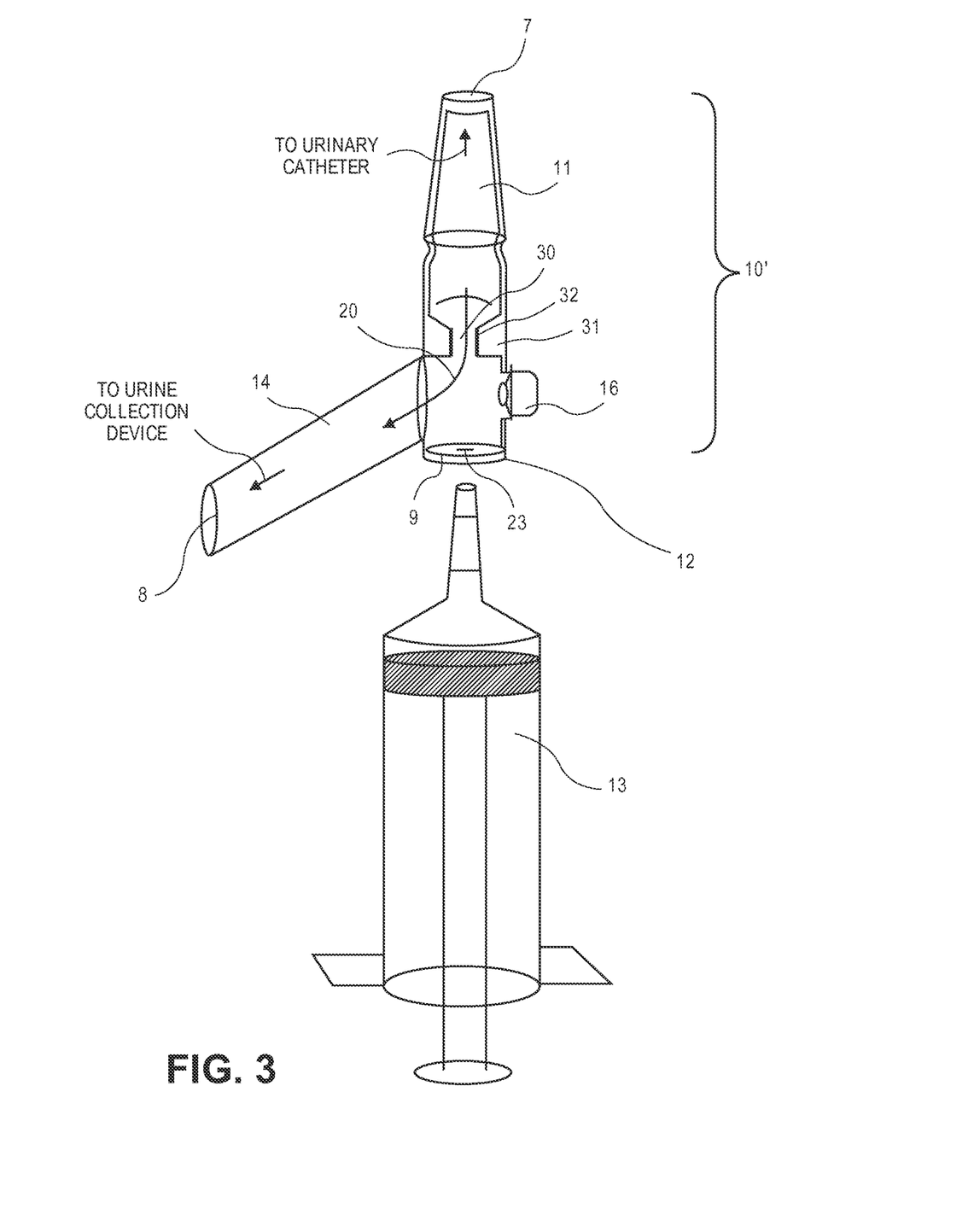
FIG. 3 is an illustration of a preferred embodiment of a self closing port and valve assembly according to another embodiment of the invention, without an irrigating syringe inserted into a self closing port so that urine can flow into a urine collection device.
Figure 4:
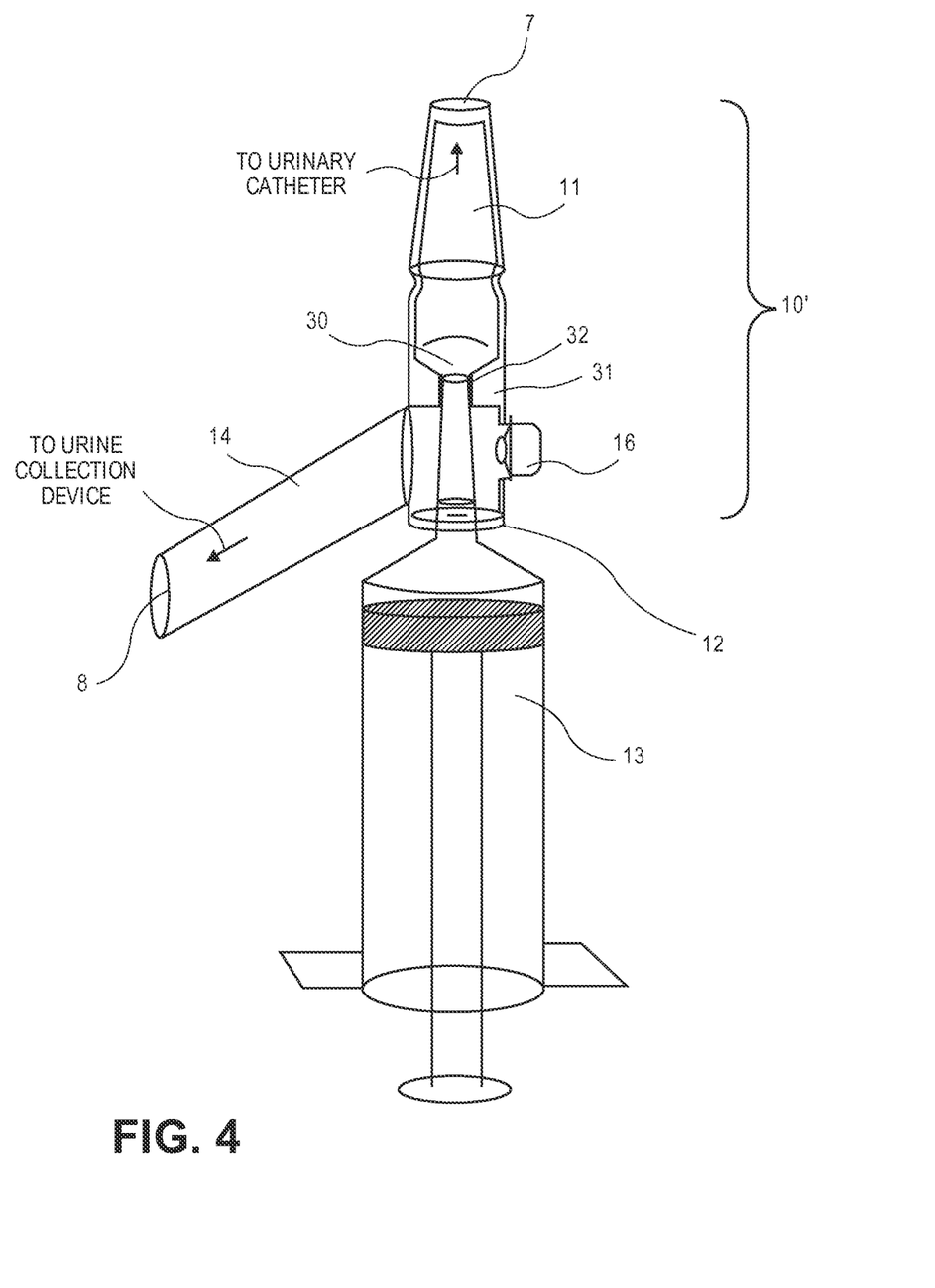
FIG. 4 is an illustration of a self closing port and valve assembly showing the device of FIG. 3 showing an irrigating syringe inserted into the self closing port and bypassing the urine collection device through means of a valve which closes flow when to urine collection device when irrigation device is attached.

FIG. 3 is an illustration of an alternative embodiment of the port and valve assembly 10'. In FIG. 3 a syringe is not inserted through a self closing port, and fluid 20 is free to flow through an internal valve 31 through an opening in the valve 30. In FIG. 4 the flow of fluid to the drainage bag is shut off when an irrigation syringe is inserted into the port and valve assembly by means of an internal valve 31 which mates with the tip of the irrigation syringe when inserted. The tip of the irrigation syringe fits snugly into the internal valve, sealing flow of fluid or air from the drainage bag.

The internal valve 31 in the embodiment of FIG. 3 and FIG. 4 is made by a thickening in the wall of the port and valve assembly, which decreases the diameter of the channel, forming the valve opening 30. The internal valve 31 created by the thickened wall may in some embodiments be lined with a flexible material such as foam, latex, or silicone to form a valve seat 32 adapted to cooperate with an exterior surface of the syringe. When an irrigation device is inserted through the irrigation port, it enters the valve opening, and the syringe compresses the expandable material 32 lining the internal valve. The syringe is held tightly in place by this compression and creates an air and fluid seal.

Figure 5:
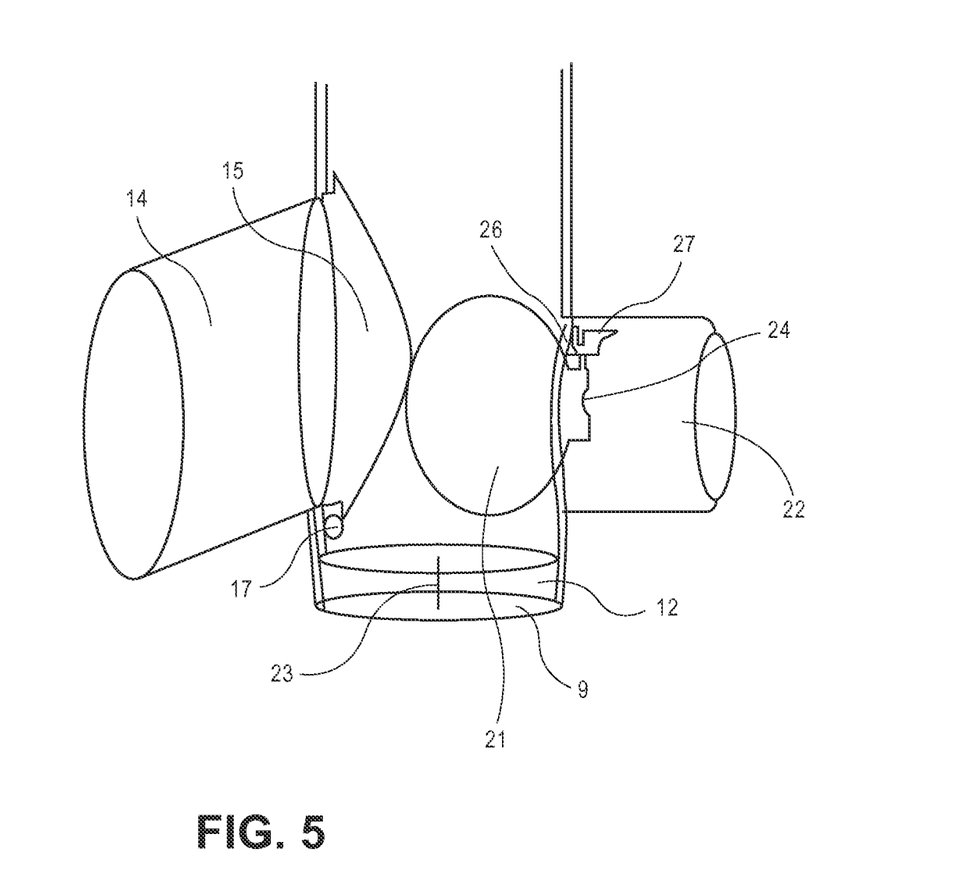
FIG. 5 is a detail of a port and valve assembly showing one embodiment of an optional valve actuator being used with the assembly shown in FIGS. 1 and 2.
Figure 7:
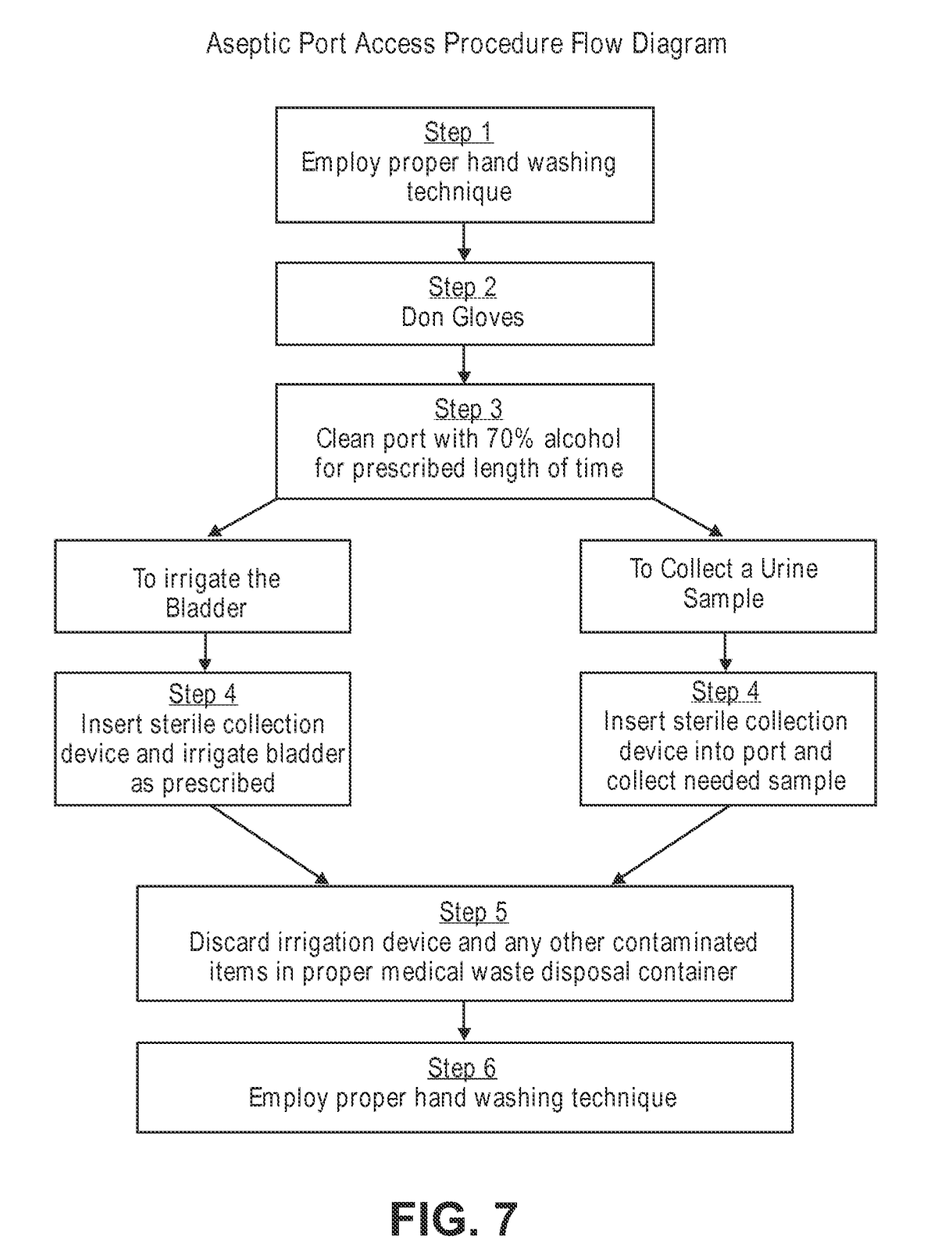
FIG. 7 is a flow diagram showing an aseptic port access procedure for irrigating or collecting a urine specimen from a port and valve assembly.

FIG. 5 shows the self closing irrigation port 12 in more detail. Irrigation port 12 has a self sealing membrane 9 made of latex or other highly flexible and pliable material. The membrane has a small pliable hole 23 within in the center which runs from the external portion to the internal portion. When a syringe or other irrigation device is pushed against the external portion of the membrane, the pliable hole 23 spreads open and the irrigation device can be passed through the membrane to the internal portion of the port. When the syringe is removed, the opening in the port closes tightly, forming a seal which keeps urine in, and bacteria out of the urinary drainage system. The flat surface of the port is easily sanitizable with 70% alcohol or other standard medical sanitizer, allowing for aseptic port access without introduction of bacteria into the drainage system. FIG. 7 is a flow diagram of an aseptic port access procedure.

The embodiment of the valve control mechanism in FIG. 5 consists of a small compliant balloon 21 which is inflated by an air filled chamber 22 which is made of a soft compressible material. By applying pressure to the air filled chamber manually, typically with the push of a finger or thumb, air is squeezed out of the chamber and into the balloon, which, in turn closes the valve stopping the flow of urine out of the bladder. The chamber is fashioned in such a way as to allow air to pass without resistance into the balloon through a one way valve 24. Once inside the balloon, the air must pass through a block 27 in which one or more holes form a balloon deflation orifice. The time period over which balloon 21 deflates can be controlled by the size and/or number of holes in block 27, which allows for control of the amount of time the valve 15 stays open. The air passes through the block and out the air exit hole 26.

Figures 6A, 6B:
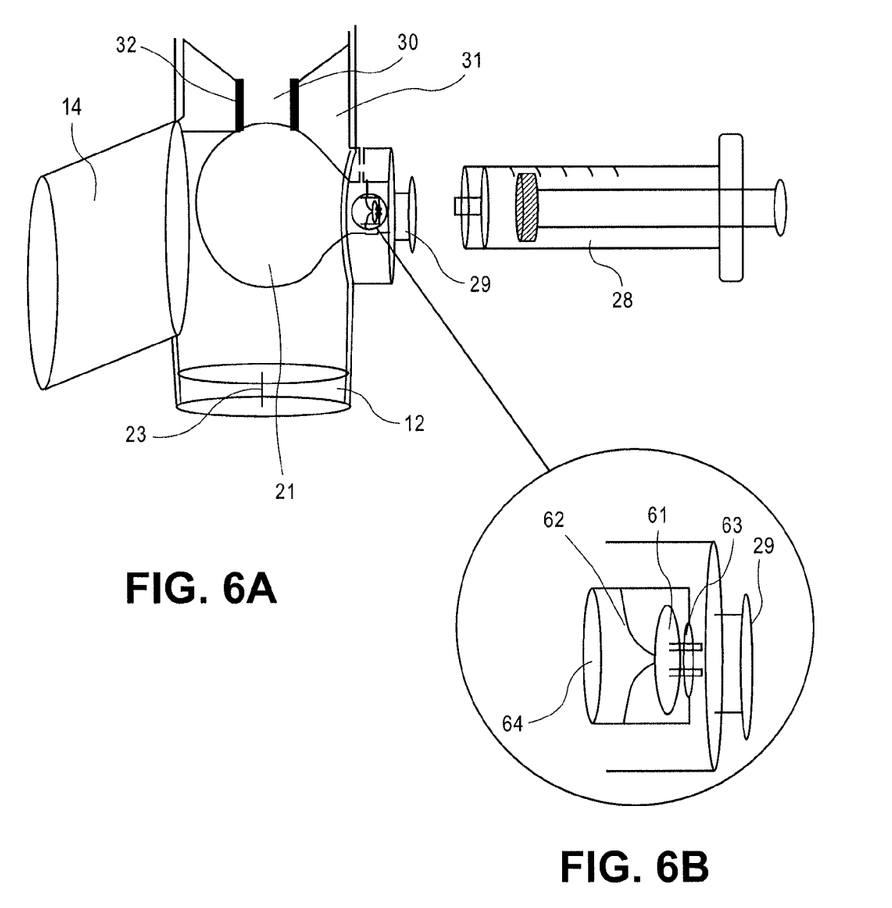
FIGS. 6A and 6B show another embodiment of an optional valve actuator being used with the assembly shown in FIGS. 3 and 4.

FIG. 6 is an illustration of an embodiment of a valve control mechanism for use with the port and valve assembly of FIGS. 3 and 4. This figure demonstrates how the balloon 21 inflates to close off the flow of fluid from the catheter to the drainage bag by blocking flow from the opening 30 to the urinary drainage end of the port and valve assembly.

In other embodiments the balloon may be inflated by other means such as a syringe. FIGS. 6A and 6B show one embodiment of the port and valve assemble in which the compliant balloon is inflated by a syringe 28. Air or fluid is introduced into the balloon by the syringe which attaches onto a luer locking connection 29, which has a valve 61 attached to a spring 62. When the syringe is attached it pushes prongs 63 on the surface of valve 61, depressing the valve and spring and opening a fluid connection between the syringe and balloon cavity 64. When the syringe is removed, the spring pushes the valve closed sealing the compartment and trapping the air or fluid within the balloon, keeping it inflated. In order to restart the flow of urine from the bladder to the urinary drainage bag, a syringe is simply re-attached to the luer locking port and the air or fluid is removed from the balloon.

In some embodiments the air in the balloon slowly leaks out through a different air passage 26 from which it entered and through a block 27 with one or more holes, as described above. The valve control mechanism 16 in some embodiments may employ a lever instead of a balloon which pushes the valve shut.

It will be apparent to a skilled artisan that the embodiments described herein are exemplary of inventions that may have greater scope than any of the singular descriptions presented. There may be alterations made in these examples without departing from the spirit and scope of the invention disclosed. For example, any aspect of an improved aseptic urinary drainage device and system may have components with different shapes or designs within different embodiments. For instance spring types, housing shape, valve diameter and compositions may vary in design from one embodiment to another, but not overall function. In some embodiments the catheter connection port may be the drainage end of a urinary catheter. In some embodiments the urine exit port may be an intrinsic part of the urine collection device, and in some embodiments the port and valve assembly may be separate from the urine collection device. These or other features may change in different embodiments.

What is claimed is:

1. A urinary catheter connector system comprising:
    a housing;
    a catheter connector port supported by the housing and configured to attach to a urinary catheter;
    a urine exit port supported by the housing and configured to connect to a urine collection device;
    an irrigation port supported by the housing and configured to receive an irrigation syringe;
    a channel in the housing fluidly connecting the catheter connector port, the urine exit port and the irrigation port;
    an internal valve supported by the housing and adapted to cooperate with the irrigation syringe to shut off flow of fluid and air to the urine exit port when the irrigation syringe is inserted and allow for flow of fluid and air to the urine exit port when the irrigation syringe is removed; and
    a valve control mechanism comprising a compliant balloon adapted to be inflated to close the internal valve, wherein the valve control mechanism further comprises a compressible fluid-filled actuation chamber, first and second passages connecting the actuation chamber with the interior of the balloon and a one-way valve disposed in the first passage to permit fluid flow from the actuation chamber into the balloon and block fluid flow from the balloon into the actuation chamber.

2. The system of claim 1 wherein the internal valve has a first position in which the urine collection device is in fluid communication with the catheter connector port and a second position in which the urine collection device is not in fluid communication with the catheter connector port.

3. The system of claim 2 wherein the internal valve is biased to the first position.

4. The system of claim 3 wherein the internal valve comprises a spring.

5. The system of claim 3 wherein the internal valve is adapted to be moved from the first position to the second position by the tip of the irrigation syringe when the tip is inserted into the irrigation port.

6. The system of claim 1 wherein the internal valve comprises a thickening in the wall of the housing, wherein said thickening decreases the diameter of the channel and is configured to approximate the size of the tip of the irrigation syringe and to mate snugly with the irrigation syringe, wherein when the irrigation syringe is inserted into the internal valve, the urine collection device is not in fluid communication with the catheter connector port, and when the syringe is not inserted into the internal valve, the urine collection device is in fluid communication with the catheter connector port.

7. The system of claim 1 wherein the internal valve comprises a valve seat adapted to mate with an exterior surface of the irrigation syringe to shut off the flow of fluid and air to the urine exit port when the irrigation syringe is inserted and allow for the flow of fluid and air to the urine exit port when the irrigation syringe is removed.

8. The system of claim 1 wherein the irrigation port connects to the channel between the catheter connection port and the urine exit port.

9. The system of claim 1 wherein the valve control mechanism further comprises a syringe port adapted to permit inflation of the balloon by a syringe.

10. The system of claim 1, wherein the irrigation port includes a pliable membrane extending thereover, the pliable membrane having a self-sealing opening therein configured to allow a tip of the irrigation syringe to extend therethrough.

11. The system of claim 10 wherein the proximal surface of the pliable membrane is flat and completely exposable to friction applied with a medical sanitizing agent so that the irrigation port is fully sanitizable.

12. The system of claim 10, wherein a distance between a proximal surface of the pliable membrane and a distal end of the internal valve is selected such that the tip of the irrigation syringe can extend from a proximal end of the self-sealing opening to the distal end of the internal valve when the irrigation syringe is inserted into the irrigation port.

* * * * *